United States Patent [19]

Moore

[11] 4,219,501

[45] Aug. 26, 1980

[54] ANTI-INFLAMMATORY METHOD

[75] Inventor: George G. I. Moore, Birchwood, Minn.

[73] Assignee: Riker Laboratories, Inc., Northridge, Calif.

[21] Appl. No.: 55,334

[22] Filed: Jul. 6, 1979

Related U.S. Application Data

[62] Division of Ser. No. 861,892, Dec. 19, 1977, Pat. No. 4,172,151, which is a division of Ser. No. 797,137, May 16, 1977, abandoned.

[51] Int. Cl.$^2$ ........................................... C07C 103/38
[52] U.S. Cl. ............................ 260/562 A; 260/562 B; 260/571; 568/747; 568/642; 424/324; 424/330; 424/340; 424/346
[58] Field of Search ..................... 260/562 B, 562 A

[56] References Cited

U.S. PATENT DOCUMENTS

| | | | |
|---|---|---|---|
| 3,711,554 | 1/1973 | Engelhardt et al. | 260/591 |
| 3,932,324 | 1/1976 | Stretanski | 260/23 H |
| 4,100,191 | 7/1978 | Fischer et al. | 260/562 A |

FOREIGN PATENT DOCUMENTS 2356520 5/1974 Fed. Rep. of Germany .
1326292 5/1963 France .

OTHER PUBLICATIONS

Efremenko et al.; Isn. Akad. Nauk SSSR, Sec. Khim, 1969 (11) pp. 2613–2615.
J. Am. Chem. Soc. 95(1973) p. 4698.
J. Org. Chem. 33(1968) p. 1245.
J. Am Chem. Soc. 79(1953) p. 5019.

*Primary Examiner*—Arthur P. Demers
*Attorney, Agent, or Firm*—Cruzan Alexander; Donald M. Sell; Donald C. Gipple

[57] ABSTRACT

Compounds in which 2,6-di(t-butyl)phenol is substituted in the 4 position by an optionally substituted phenyl group have valuable pharmacological activity as anti-inflammatory agents.

3 Claims, No Drawings

ANTI-INFLAMMATORY METHOD

This is a division of copending application Ser. No. 861,892 filed Dec. 19, 1977 now U.S. Pat. No. 4,172,151, Ser. No. 861,892 being a division of copending application Ser. No. 797,137 filed May 16, 1977 (now abandoned).

BACKGROUND OF THE INVENTION

This invention relates to the use of 2,6-di(t-butyl)-4-phenylphenols as anti-inflammatory agents and to certain novel compounds.

The compound 2,6-di(t-butyl)-4-phenylphenol itself is known (see, for example, J. Am. Chem. Soc. 95:4698, 1973), and the synthesis of 2,6-di(t-butyl)-4-(4'-nitrophenyl)phenol has been reported (J. Org. Chem. 33:1245, 1968). 2,6-Di(t-butyl)-4-phenylphenols in which the 4-phenyl ring is substituted by other groups are, however, novel insofar as is known. No physiological use of any of these compounds has been reported, however.

DETAILED DESCRIPTION OF THE INVENTION

Specifically the invention relates to a method for combatting inflammatory processes in mammalian animals which comprises administering thereto an effective dose, less than the toxic amount, of a compound of the formula:

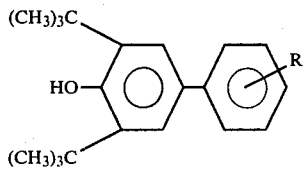

wherein R is selected from hydrogen, amino, alkanamido containing from 2 to 4 carbon atoms, trifluoroacetamido, halogen, methoxy, methyl and 4-nitro. The invention also relates to anti-inflammatory compositions comprising one or more such compounds (in which R is as just recited) together with a suitable pharmaceutical extending medium. The compounds of formula I wherein R is hydrogen, amino or methoxy are presently preferred for use in the anti-inflammatory method and compositions of the invention, particularly those in which R is hydrogen, 4'-amino or 2'-methoxy.

In another aspect, the invention relates to new chemical compounds of structure I but wherein R is amino, alkanamido containing from 2 to 4 carbon atoms or trifluoroacetamido. It is noted that when R is nitro, only the compound wherein R is 4'-nitro has been found to be useful as an anti-inflammatory agent. Novel compounds wherein R is 2'-nitro or 3'-nitro form part of the invention, however, since they can be reduced to 2'-amino or 3'-amino compounds which are useful as anti-inflammatory agents.

In addition to their anti-inflammatory activity, some of these compounds are also analgesic and antipyretic agents and some have mild immunosuppressant activity.

In order to determine and assess pharmacological activity, testing in animals is carried out using various assays known to those skilled in the art. Thus, the anti-inflammatory activity of the compounds can be conveniently demonstrated using an assay designed to test the ability of these compounds to antagonize the local edema which is characteristic of the inflammatory response (the rat foot edema test). Anti-inflammatory activity may also be detected by other assays known to the art such as the cotton pellet granuloma test and the adjuvant arthritis test and the inhibition of the enzyme prostaglandin synthetase.

Leading references to the rat foot edema method are:

(1) Adamkiewicz et al, Canad. J. Biochem. Physio. 33:332, 1955;

(2) Selye, Brit. Med. J. 2:1129, 1949; and (3) Winter, Proc. Exper. Biol. Med. 111:554, 1962.

The edema test is performed on adult female rats. One group of 10 rats serves as non-medicated controls, while another group of 10 rats receives the test compound at various times prior to the induction of the edema, usually 15 minutes, one hour and/or 18 hours. The test compound is administered orally as a suspension in 4 percent aqueous solution of acacia. Edema is induced by the plantar injection of 0.5 percent carrageenin (0.1 ml/foot) into the right hind foot. The left hind foot receives a like volume of 0.9 percent saline solution. One hour later, the volume of each hind foot is determined plethysmographically. The edema is expressed as the increase in the volume of the edemogen-injected foot (volume of the "edemogen foot" less the volume of the "saline foot"). The percent inhibition is calculated by dividing the mean increase in the edema of the edemogen foot of the medicated group by the mean increase in the non-medicated group, multiplied by 100. An active dose is that giving a statistically significant inhibition of the induced edema, usually in the range of about 25–35 percent inhibition.

The compounds are preferably administered orally as anti-inflammatory agents but other known methods of administration are contemplated as well, e.g. dermatomucosally (for example dermally, rectally and the like) and parenterally, for example by subcutaneous injection, intramuscular injection, intra-articular injection, intravenous injection and the like. Ocular administration is also included. Dosages ordinarily fall within the range of about 1 to 500 kg/mg of body weight of the mammal to be treated although oral dosages are not usually above 100 mg/kg. Suitable forms for oral administration include liquids (such as 4 percent acacia and polyethylene glycol solutions), tablets (which may contain anhydrous lactose, microcrystalline cellulose, modified starch, calcium stearate and talc, as well as other conventional compounding agents together with the active anti-inflammatory agents), solid suspensions and capsules. Suitable carriers for topical application include creams, gels, tapes and the like. Liquid formulations, such as solutions or suspensions of the active ingredient in inert carriers, are contemplated for dosage by injection.

The compounds which are presently preferred for use in the process of the invention (due to their high activity in the rat foot edema test) are:

2,6-di(t-butyl)-4-phenylphenol, 4-(4'-aminophenyl)-2,6-di(t-butyl)phenol and 2,6-di(t-butyl)-4-(2'-methoxyphenyl)phenol.

The preparation of compounds of the invention may be carried out as described in the prior art or by chemical reaction of compounds described in the prior art. Alternatively, novel compounds of the invention, for example, compounds wherein R is amino, may be further utilized as intermediates to prepare other compounds of the invention. Many compounds of the invention are conveniently prepared by reaction of 2,6-di(t-butyl)benzoquinone with an appropriate Grignard reagent, followed by reduction of the intermediate substituted cyclohexadienone. The necessary starting materials are well known to the art. The reduction step may be carried out using hydrogen gas and a catalyst such as palladium on charcoal or Raney nickel, using a metal hydride reducing agent such as lithium aluminum hydride or using hydrogen iodide.

Conventional reactions of aromatic substituent groups are generally applicable to the compounds of the invention. For example, nitro groups can be reduced, amino groups can be acylated, amino groups can be diazotized and replaced and the like.

Preparation of novel compounds of the invention and known compounds useful in the method of the invention are described in the following illustrative examples.

EXAMPLE 1

Magnesium metal (0.55 g.) and 50 ml. of diethyl ether are treated with a few ml. of a solution of 4.25 g. of 4-bromoanisole in 50 ml of ether. An iodine crystal is added, and the mixture begins to react upon warming. The remainder of the solution is added, and the mixture is heated at its reflux temperature for 15 minutes. It is then added over 30 minutes to a solution of 2,6-di(t-butyl)benzoquinone in 50 ml. of ether. This mixture is heated at its reflux temperature for two hours, then stirred at room temperature for 16 hours. The product is 2,6-di(t-butyl)-4-hydroxy-4-(4'-methoxyphenyl)-2,5-cyclohexadienone.

To this product is added 1.5 g. of lithium aluminum hydride dissolved in diethyl ether. After stirring for 30 minutes, the solution is acidified with 10 percent hydrochloric acid and extracted with dichloromethane. The extracts are dried over magnesium sulfate, then evaporated to provide an oil which is chromatographed on 125 g. of 60–200 mesh silica gel, eluting with 1:3 benzene-hexane. The first 500 ml. of solvent is evaporated to provide an oil which crystallizes when petroleum ether is added. Recrustallization from petroleum ether provides 2,6-di(t-butyl)-4-(4'-methoxyphenyl)phenol, m.p. 109°–110° C.

| Analysis: | % C | % H |
|---|---|---|
| Calculated for $C_{21}H_{28}O_2$: | 80.7, | 9.0 |
| Found: | 80.9 | 9.2 |

EXAMPLE 2

Using the method described in the art (J. Org. Chem. 33:1245, 1968) 2,6-di(t-butyl)-4-(4'-nitrophenyl)phenol, m.p. 154°–156° C., is prepared. Using this method and starting with 2-chloronitrobenzene, 2,6-di(t-butyl)-4-(2'-nitrophenyl)phenol, m.p. 101°–102.5° C. is prepared.

EXAMPLE 3

A solution of 50 g. (0.152 mole) of 2,6-di(t-butyl)-4-(4'-nitrophenyl)phenol in 350 ml. of ethyl acetate is reduced with hydrogen gas at about 45 psig in a Paar apparatus using 10 percent palladium on charcoal as catalyst. The mixture is allowed to stand for about 16 hours, filtered, and the filtrate evaporated under vacuum. The residue is cooled, dissolved in ethanol and triturated with water. The resulting off-white solid is recrystallized from petroleum ether to provide 4-(4'-aminophenyl)-2,6-di(t-butyl)phenol, m.p. 113°–114.5° C.

| Analysis: | % C | % H | % N |
|---|---|---|---|
| Calculated for $C_{20}H_{27}NO$: | 80.7, | 9.1, | 4.7 |
| Found: | 80.1, | 9.1, | 4.7. |

EXAMPLE 4

A solution of 10 g. (0.0336 mole) of 4-(4'-aminophenyl)-2,6-di(t-butyl)phenol in 50 ml. of dichloromethane is reacted with 7.1 g. (0.034 mole) of trifluoroacetic anhydride. The immediate reaction is followed by evaporation of the solvent to provide a residue which is recrystallized from a benzene-hexane mixture. The white product is 2,6-di(t-butyl)-4-(4'-trifluoroacetamidophenyl)phenol, m.p. 155°–156° C.

| Analysis: | % C | % H | % N |
|---|---|---|---|
| Calculated for $C_{22}H_{26}F_3NO_2$: | 67.1, | 6.7, | 3.6 |
| Found: | 67.1, | 6.7, | 3.5. |

EXAMPLE 5

A solution of 15 g. (0.050 mole) of 4-(4'-aminophenyl)-2,6-di(t-butyl)phenol in 100 ml. of glacial acetic acid is treated with 5.2 g. (0.050 mole) of acetic anhydride. The resulting solution is heated gently for 10 minutes, diluted with water, cooled, and the solid product is separated by filtration. Recrystallization from a benzene-hexane mixture provides 4-(4'-acetamidophenyl)-2,6-di(t-butyl)phenol, m.p. 173°–174.5° C.

| Analysis: | % C | % H | % N |
|---|---|---|---|
| Calculated for $C_{22}H_{29}NO_2$: | 77.8, | 8.6, | 4.1 |
| Found: | 77.8, | 8.8, | 4.0. |

EXAMPLE 6

To a stirred solution of 15 g. (0.0504 mole) of 4-(4'-aminophenyl)-2,6-di(t-butyl)phenol in 75 ml. of dichloromethane is added dropwise 5.37 g. (0.0504 mole) of n-butyroyl chloride. The reaction is immediate. The solvent is removed by evaporation, and the solid residue is recrystallized, first from aqueous ethanol, then from heptane to provide 4-(4'-butyramidophenyl)-2,6-di(t-butyl)phenol, m.p. 180°–181° C.

| Analysis: | % C | % H | % N |
|---|---|---|---|
| Calculated for $C_{24}H_{33}NO_2$: | 78.4, | 9.0, | 3.8 |
| Found: | 78.4, | 8.9, | 3.7. |

EXAMPLE 7

Using the method described in Example 1, 2-bromomethoxybenzene is reacted with 2,6-di(t-butyl)hydroquinone to provide 2,6-di(t-butyl)-4-hydroxy-4-(2'-methoxyphenyl)-2,5-cyclohexadienone. This product is dissolved in ethanol and reduced with hydrogen gas on a Parr apparatus using palladium on charcoal as the catalyst. The white solid product is recrystallized from benzene to provide 2,6-di(t-butyl)-4-(2'-methoxyphenyl)phenol, m.p. 98.5°–100° C.

| Analysis: | % C | % H |
|---|---|---|
| Calculated for $C_{21}H_{28}O_2$: | 80.7, | 9.0 |
| Found: | 81.1, | 9.1. |

EXAMPLE 8

Using the method of Example 7, but starting from 3-bromomethoxybenzene, one obtains 2,6-di(t-butyl)-4-(3'-methoxyphenyl)phenol, m.p. 96°–98° C.

| Analysis: | % C | % H |
|---|---|---|
| Calculated for $C_{21}H_{28}O_2$: | 80.7, | 9.0 |
| Found: | 80.9, | 9.2. |

EXAMPLE 9

Using the method of Example 1, but starting from 2-bromotoluene, one obtains 2,6-di(t-butyl)-4-hydroxy-4-(2'-methylphenyl)-2,5-cyclohexadienone, m.p. 168°–171° C. This product is reduced as described in Example 7 to provide 2,6-di(t-butyl)-4-(2'-methylphenyl)phenol, m.p. 85.5°–87.5° C.

| Analysis: | % C | % H |
|---|---|---|
| Calculated for $C_{21}H_{28}O$: | 85.1, | 9.5 |
| Found: | 84.7, | 9.5. |

EXAMPLE 10

Using the method described in Example 1, 4-bromofluorobenzene is reacted to provide 2,6-di(t-butyl)-4-hydroxy-4-(4'-fluorophenyl)-2,5-cyclohexadienone, m.p. 123°–125° C. This product is reduced as described in Example 1 to provide 2,6-di(t-butyl)-4-(4'-fluorophenyl)phenol, m.p. 97°–99° C.

| Analysis: | % C | % H |
|---|---|---|
| Calculated for $C_{20}H_{25}FO$: | 80.0, | 8.4 |
| Found: | 79.7, | 8.5. |

EXAMPLE 11

Using the method of Example 7, 4-bromotoluene is converted to 2,6-di(t-butyl)-4-(4'-methylphenyl)phenol, m.p. 119.5°–121° C.

| Analysis: | % C | % H |
|---|---|---|
| Calculated for $C_{21}H_{28}O$: | 85.1, | 9.5 |
| Found: | 85.2, | 9.5. |

EXAMPLE 12

Using the method of Example 1, 2-bromochlorobenzene is reacted to provide 2,6-di(t-butyl)-4-(2'-chlorophenyl)-2,5-cyclohexadienone. This product (5.0 g., 0.015 mole) is treated with 125 ml. of concentrated hydroiodic acid and stirred for about 16 hours. The mixture is filtered, the residue rinsed with water and then dried to provide an off-white powder. The product is recrystallized from petroleum ether to provide 2-(2'-chlorophenyl)-2,6-di(t-butyl)phenol, m.p. 89.5°–91° C.

| Analysis: | % C | % H |
|---|---|---|
| Calculated for $C_{20}H_{25}ClO$: | 75.8, | 7.95 |
| Found: | 76.1, | 8.1. |

EXAMPLE 13

To a solution of 7.0 g. (0.0235 mole) of 4-(4'aminophenyl-2,6-di(t-butyl)phenol in 3 ml. (0.0706 mole) of concentrated sulfuric acid is added about 15 ml. of water, and the mixture is chilled to about 5° C. To this mixture a cold solution (about 5° C.) of 1.62 g. (0.0235 mole) of sodium nitrite in 8 ml. of water is added dropwise with stirring. The mixture is stirred for another ten minutes, and a cold solution of 3.37 g. (0.0235 mole) of cuprous bromide in 20 ml. of 48 percent hydrobromic acid is added slowly. After stirring for an additional hour, the mixture is extracted with about 100 ml. of dichloromethane. The extracts are dried, then evaporated. The residue is mixed with heptane, then filtered to provide a solid product which is purified by dissolving in hexane, eluting through a silica gel column with methanol-water and recrystallized from petroleum ether. The product is 4-(4'-bromophenyl)-2,6-di(t-butyl)phenol, m.p. 139.5°–141° C.

| Analysis: | % C | % H |
|---|---|---|
| Calculated for $C_{20}H_{25}BrO$: | 66.5, | 7.0 |
| Found: | 66.6, | 7.2. |

What is claimed is:

1. A compound of the formula

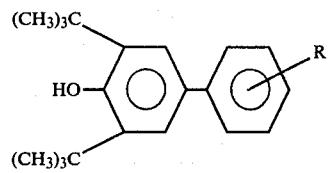

wherein R is selected from alkanamido of 2 to 4 carbon atoms and trifluoroacetamido.

2. A compound according to claim 1 wherein R is alkanamido of 2 to 4 carbon atoms.

3. A compound according to claim 1 wherein R is trifluoroacetamido.

* * * * *